United States Patent [19]
Berger

[11] Patent Number: 4,862,526
[45] Date of Patent: Sep. 5, 1989

[54] PORTABLE VAPOUR BATH

[76] Inventor: Franz R. Berger, 2745 Islington Ave., Islington, Ontario, Canada, M9V 5C1

[21] Appl. No.: 129,338

[22] Filed: Dec. 3, 1987

Related U.S. Application Data

[63] Continuation of Ser. No. 876,249, Jun. 19, 1986, abandoned.

[51] Int. Cl.$^4$ ............................................. A61H 33/06
[52] U.S. Cl. ......................................... 4/53.6; 4/531; 4/525
[58] Field of Search .................... 4/524, 525, 526, 527, 4/528, 531, 535, 536; D 24/37; 128/367, 368, 371, 373, 374, 375

[56] References Cited

U.S. PATENT DOCUMENTS

| D. 189,951 | 3/1961 | Cosper . | |
|---|---|---|---|
| D. 203,788 | 2/1966 | Plantholt | D 24/37 |
| 44,836 | 10/1863 | Heinvich . | |
| 55,194 | 5/1866 | Young . | |
| 158,022 | 12/1874 | Bremond . | |
| 348,923 | 9/1886 | Munro . | |
| 3,009,165 | 11/1961 | Washam et al. . | |
| 4,137,574 | 2/1979 | Collins | 4/526 |
| 4,340,981 | 7/1982 | Vanags | 4/536 |
| 4,432,103 | 2/1984 | Hunziker | 4/525 |

FOREIGN PATENT DOCUMENTS

| 927051 | 5/1973 | Canada . |
| 3139930 | 3/1985 | Fed. Rep. of Germany . |
| 1058731 | 2/1967 | United Kingdom . |
| 1418865 | 12/1975 | United Kingdom . |
| 2063665 | 6/1981 | United Kingdom . |

*Primary Examiner*—Henry J. Recla
*Assistant Examiner*—Linda J. Sholl
*Attorney, Agent, or Firm*—Ivor M. Hughes

[57] ABSTRACT

A portable vapor bath comprising a contoured superstructure and interior having a top, bottom, front, rear and plurality of sides; having disposed upon its front an opening closed by a closure member; said front and rear having a top and bottom said front and rear extending in planes substantially diverging from one another proximate the top of the vapor bath to a position intermediate the top and bottom of said vapor bath whereat said front and rear extend in planes substantially converging towards one another proximate the bottom of the vapor bath, said front being inclined from said top at an angle to both the normal horizontal and vertical planes away from the rear to a position intermediate its top and bottom and thereafter sloping to its bottom at an angle to both the normal horizontal and vertical planes in the opposite direction towards the rear; the rear sloping from its top at an angle to both the normal horizontal and vertical planes towards a position intermediate its top and bottom away from the front and thereafter sloping to its bottom in the opposite direction at an angle to both the normal horizontal and vertical planes, towards the front; having disposed in its top an opening located above a seating means disposed upon the bottom of the vapor bath; having affixed adjacent the bottom thereof a separate source of wet or dry heat, wherein said bottom portion has at least one opening to allow entry of said wet or dry heat into the vapor bath; wherein said portable vapor bath will, because of its contoured shape, ensure close contact of wet or dry heat forwardly, rearwardly, left and right, with the user's body located within the bath chamber upon a seat securely fastened to the interior bottom of said superstructure.

11 Claims, 4 Drawing Sheets

PORTABLE VAPOUR BATH

This is a continuation of Ser. No. 876,249, filed June 19, 1986, now abandoned.

FIELD OF THE INVENTION

This invention relates to vapour or hot air baths and more particularly to those which are portable.

BACKGROUND OF THE INVENTION

Sauna and steam baths of a multiplicity of designs in general are well known. They may be designed and constructed for simultaneous use by one or more individuals.

Baths for general use may be built into the interior of, for example, health clubs. Such installations are generally known as fixed saunas (Fin-saunas) being constructed primarily of wood, and being permanently installed in institutions and homes alike. Fixed saunas are expensive to install and once installed cannot be relocated without great expense. Further, in fixed saunas, individuals with health problems, for example, asthma or high blood pressure, must be extremely cautious in protecting themselves from overexposure. Disinfecting a wooden sauna is also a very difficult task.

Alternatively, vapour baths designed for the individual are also available and known in the art. U.S. Pat. No. Design 189,951 discloses such a "Steam Bath Cabinet" which has a very simple appearance. U.S. Pat. No. 4,340,981 at the other end of the spectrum of units available, describes very elaborate "Bathing Devices" having a multiplicity of components. Many such devices exist in varying degrees of complexity, dating as far back as 1866 as taught in U.S. Pat. No. 55,194, disclosing a vapour bath of extremely simple structure but having a questionable efficiency. Improvements were introduced with U.S. Pat. No. 158,022 which fully enclosed the individual in a cabinet, but said cabinet was no longer portable. Thence, U.S. Pat. No. 348,923 and Canadian Pat. No. 44,836 evolved. Many attempts have been made to improve such baths, developing much more complex structures, for example, British Pat. No. 1,058,731, U.S. Pat. No. 3,009,165, Canadian Pat. No. 927,051, British Pat. Nos. 1,418,856, 1,041,115 and United Kingdom Patent Application No. 2,063,665.

Applicant is also aware of application No. 3,139,930 which is before the German Patent Office and covers the same subject matter, which teaches a portable sauna bath structure similar in construction to U.S. Pat. No. Design 189,951, marketed by "Sauna Fit" within the country.

However, in spite of all the aforementioned teachings, a void currently exists within the technology for a fully portable, lightweight, economical and transportable vapour bath which is efficient, yet simple to operate and disinfect, which is not taught within any of the aforementioned references cited.

It is therefore an object of this invention to provide a portable vapour bath which is simple to use yet efficient in design and requiring no installation.

It is a further object of this invention to provide a vapour bath which is fully portable requiring no permanent or temporary piping connected thereto.

It is a further object of this invention to provide a vapour bath that is safe to use having all electrical connections external to the occupied bath unit itself, wherein one does not feel confined or oppressed while using the bath.

It is still a further object of this invention to provide a vapour bath that is lightweight in construction, yet rugged in design.

It is also a further object of this invention to provide a vapour bath having effective contoured shaping, making efficient use of steam even at remote extremities of the body while allowing for the comfort of even the largest of individuals.

It is still a further object of this invention to provide a vapour bath wherein the user's head is precluded allowing a continual supply of fresh air to the lower extremities of the body.

Further and other objects of this invention will become apparent to a man skilled in the art when considering the following summary of the invention and the more detailed embodiments of the invention illustrated herein.

SUMMARY OF THE INVENTION

To these ends, according to one aspect of the invention, a portable vapour bath is provided comprising a double-tapered contoured superstructure and interior (in a preferred embodiment being constructed from fibreglass-reinforced plastic), having a top, bottom, front, rear and plurality of sides, having disposed upon its front an opening closed by a closure member said closure member being disposed at an angle to both the normal horizontal and vertical planes; said front and rear having a top and bottom, said front and rear extending in planes substantially diverging from one another each plane diverging from the normal vertical plane proximate the top of the vapour bath to a position intermediate the top and bottom of said vapour bath whereat said front and rear extend in planes substantially converging towards one another proximate the bottom of the vapour bath, said front being inclined from said top at an angle to both the normal horizontal and vertical planes away from the rear to a position intermediate its top and bottom and thereafter sloping to its bottom at an angle to both the normal horizontal and vertical planes in the opposite direction towards the rear; the rear sloping from its top at an angle to both the normal horizontal and vertical planes towards a position intermediate its top and bottom away from the front and thereafter sloping to its bottom in the opposite direction at an angle to both the normal horizontal and vertical planes towards the front; having disposed in its top an opening located above a seating means disposed upon the bottom of the vapour bath; having affixed adjacent the bottom thereof a separated source of wet or dry heat, wherein said bottom portion has at least one opening to allow entry of said wet or dry heat into the vapour bath; wherein said portable vapour bath will because of its contoured shape, said contouring providing diverging and converging planes to ensure close contact of wet or dry heat forwardly, rearwardly, top and bottom, with the user's body located within the bath chamber upon a seat securely fastened to the interior bottom of said superstructure preferably having the plurality of sides comprising at least one member per side, said sides having a top and bottom left and right, the sides sloping from their tops towards a position intermediate their tops and bottoms away from the opposite side thereof and thereafter sloping to their bottoms in the opposite direction towards the opposite side, the sides further sloping from their left towards a position intermediate its left and right away from the opposite side, and thereafter sloping to their right in the opposite direction towards the opposite side; wherein said portable vapour bath will because of its contoured shape said contouring diverging and converging planes, ensure close contact of wet or dry heat forwardly, rearwardly, bottom, top, left and right, with the user's body located within the bath chamber upon a seat securely fastened to the interior bottom of said superstructure.

Preferably, the bottom of the vapour bath is constructed to rigidify the superstructure by resiliently inter-connecting said front, rear and sides. In one embodiment the bottom is convexly shaped. The superstructure describes within its interior surfaces a bathing chamber accessed through the closure member upon the front of said vapour bath and containing within said bathing chamber alternatively fastened upon its bottom a centrally-located seating device.

In a preferred embodiment, externally fastened to the rear of the superstructure at the bottom thereof is a source of wet or dry heat, and in a preferred embodiment, an electrically-operated, thermostatically-controlled vapour generator having a multiplicity of orifices disposed upon its fastened surface compatibly aligned with orifices upon the superstructure of the vapour bath, said generator having a water tank (normally containing four to six liters of water in a preferred embodiment) within which an insulated thermostatically submersible coil is contained which generates vapour at 40 degrees to 45 degrees Celsius to a limit of two-thirds of the capacity of the water tank as a precautionary measure to prevent overheating. The vapour generated exits the vapour generator at the orifices disposed upon its affixed outer surface and enters the bathing chamber through compatibly-aligned holes within the superstructure of the vapour bath, said compatibly-aligned holes having adjustable diameters to increase or reduce the volume of vapour entering the bath chamber and controlling the velocity of said vapour entry.

The seat, centrally located within the bath chamber, may alternatively be embodied with back and arm rests and alternative means for adjusting the height thereof depending on the physical makeup of the user. Further recesses may be manufactured within the interior or exterior superstructures of the vapour bath to provide for ledges, footrests, soap dishes, hooks etc. In an alternative embodiment, dolly wheels may be affixed to the vapour bath to permit easy transport of the unit from room to room, and/or a tilting device or levelling legs may be incorporated therein. Further, hot and/or cold water may be provided for showering purposes.

DETAILED DESCRIPTION OF THE DRAWINGS

Figure 1:
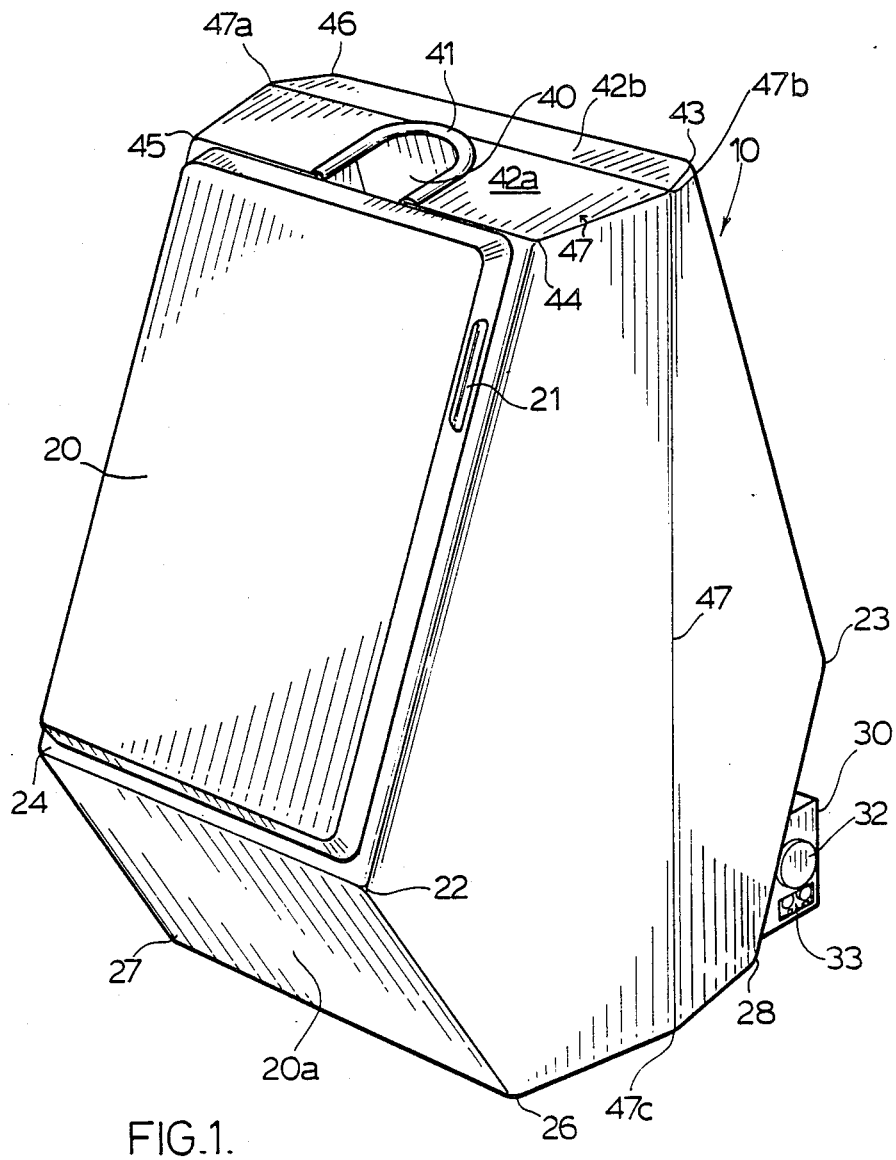
FIG. 1 is a perspective view of the portable vapour bath in a preferred embodiment of the invention.
Figure 2:
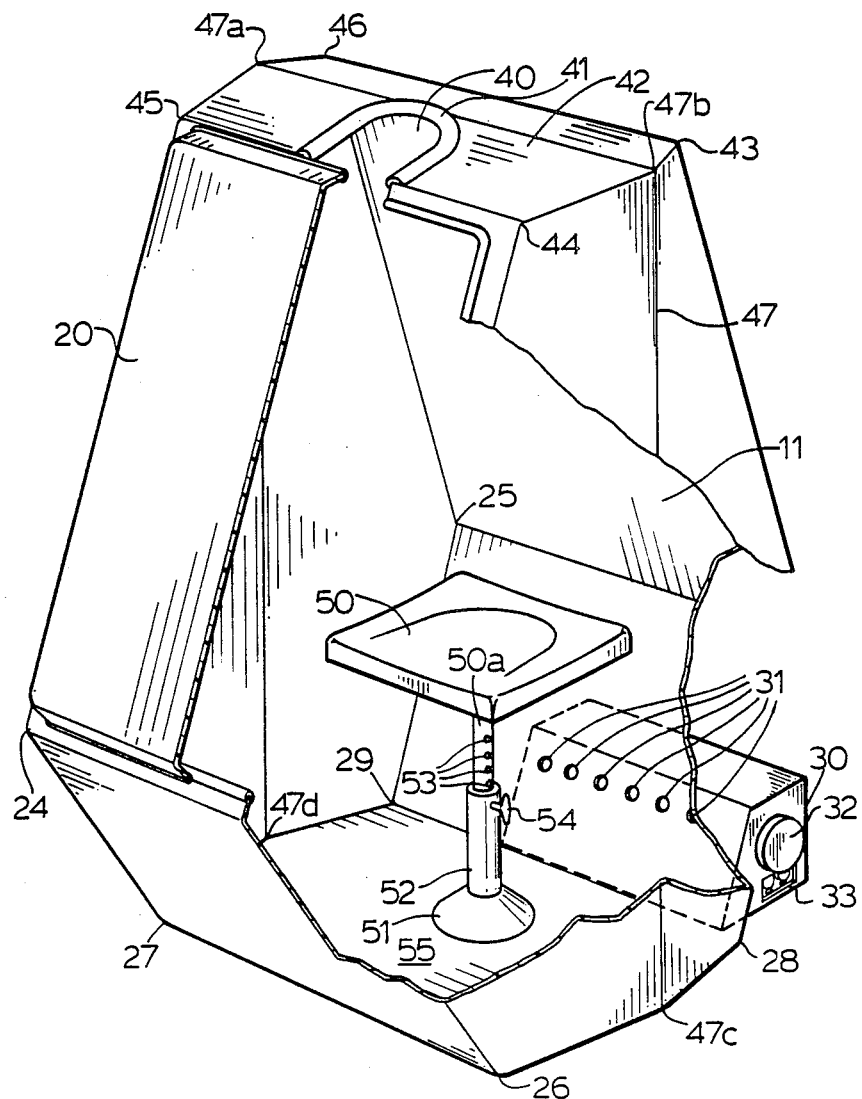
FIG. 2 is a perspective view of the portable vapour bath cut away to reveal the internal chamber and the components therein in a preferred embodiment of the invention.
Figure 5:
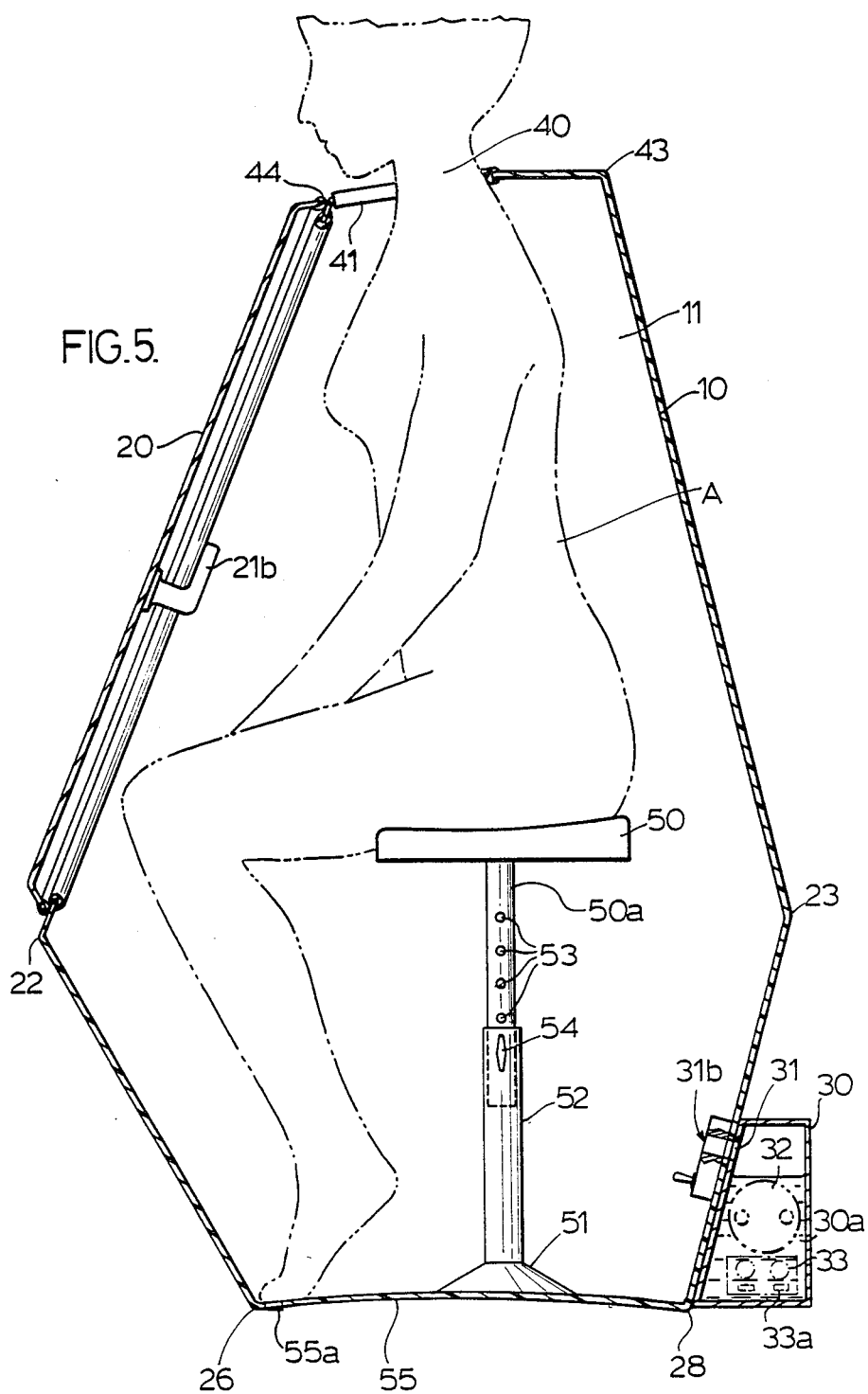
FIG. 5 is a side view of the portable vapour bath cut away to reveal the contoured shape thereof and the positioning of an individual within in a preferred embodiment of the invention.

Referring now to the drawings depicting a preferred embodiment of the invention, in FIGS. 1 and 2 a vapour bath 10 is illustrated having a fiberglass reinforced plastic body of contoured shape, having a front, top, bottom, rear and two sides defining within a bath chamber 10, having at its front a door frame wherein is fastened a seal against which is affixed a sealable door 20 with exterior and interior handle members 21 and 21($b$), said door 20, inclined at an alternative angle to both the horizontal and vertical planes, having adjacent its top a neck opening 40 having padding 41, thereupon for an individual head to be extended comfortably and securely through said door, having adjacent its bottom a retaining wall 20($a$) circumlimited by corners 22, 24, 26 and 27 respectively, said wall inclining downwardly away from the door 20 extending from corners 22 and 24 to corners 26, 27 which forwardly support the vapour bath, said vapour bath 10 having a top 42 comprising two panels 42($a$) and 42($b$) slightly angled to each other and joining at circumscribing rigidifying edge or seam 47, wherein panel 42($a$) centrally containing at least one rearwardly-extending neck opening 40 slightly more inclined downwardly away from the horizontal panel 42($b$) to allow for the proper fit of neck opening 40 and neck padding 41 when vapour bath 10 is in use as best illustrated in FIG. 5. It should be noted that neck opening 40 is defined on three sides only having a void at its front adjacent door 20; said vapour bath 10 having two sides, each side comprising two panels slightly inclined outwardly away from circumscribing, rigidifying edge or seam 47, further contouring vapour bath, said panels being described by corners (i) 26, 22, 44, 47($b$) and 47($c$), (ii) 47($c$), 47($b$), 43, 23, and 28, (iii) (as best illustrated in FIG. 2) 27, 24, 45, 47($a$) and (iv) 47($d$), 47($a$), 46, 25 and 29; said vapour bath having a bottom and rear as best illustrated in FIG. 2 and having affixed upon its rear near the bottom a vapour being described by corners 26, 27, 47($d$), 29, 28 and 47($c$) and having upon its interior surface floor 55 and said rear being described by two adjacent panels top and bottom slightly inclined to each other as defined by corners 46, 43, 23 and 25 for the top panel and 25, 23, 28 and 29 for the bottom panel, said bottom rearward panel being complementary to panel 20($a$) upon the front of vapour bath 10, said rearward bottom panel having insulated vapour generator 30 affixed thereto, wherein vapour ports 31 of vapour unit 30 align with adjustable inlet ports 31($b$) described through the rearward bottom panel, as best illustrated in FIG. 5, thereby allowing hot air, steam, or medicated vapours to safely enter the bathing compartment 11 without exposing the bather to a risk of electrical shock, wherein a bather safely sits upon at least one adjustable contoured seat 50 which may alternatively have a back rest and arm rests, wherein affixed to the bottom of seat 50 is support column 50($a$) wherein is described an alternative number of holes 53 into which height adjustment lever 54 of base support 52 (attached to footing member 51 affixed to floor 55) is alternatively engaged; said vapour generator 30 being separate, having upon its outward surface, controls 33 for heating core 32 which is thermostatically controlled to prevent overheating of the vapour beyond 40 degrees Celsius, or continual operation when the supply of water is too low to effectively generate steam. The floor 55 may be convex in shape allowing water to the corners wherein a plug or drain may be provided.

Figure 3:
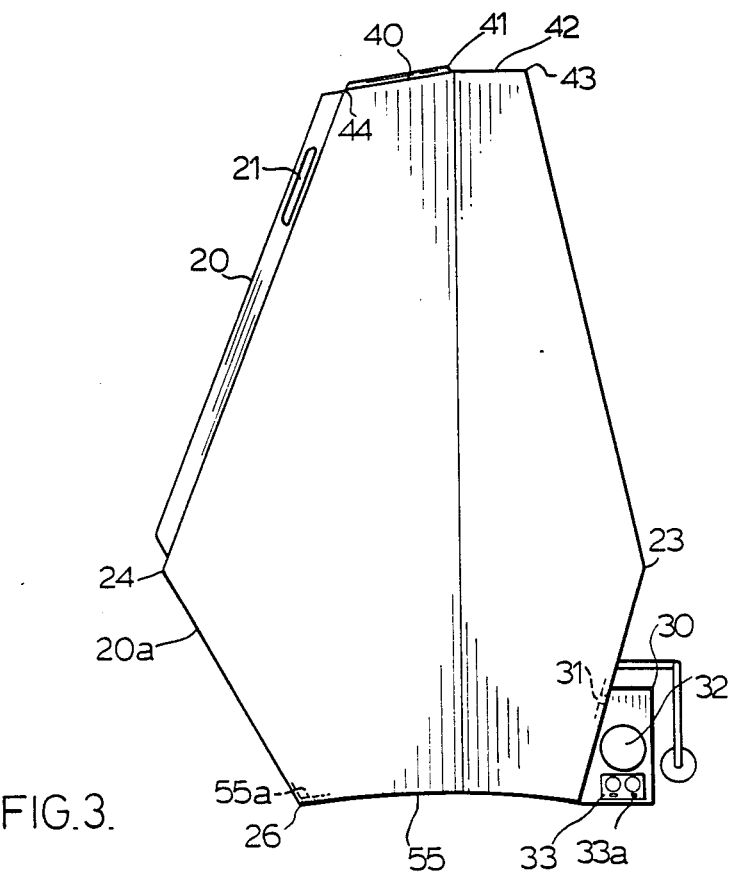
FIG. 3 is a top view of the portable vapour bath in a preferred embodiment of the invention.

Referring now to FIG. 3 wherein vapour bath unit 10 is illustrated in side view, the contoured shape of both the front wall and rear wall panels and the location of vapour generator 30 is illustrated. Further the stabilizing convex shape of floor 55 is illustrated having in one alternative embodiment a drain to allow quick and easy sanitation and disinfecting of the vapour bath from time to time. As illustrated, the upper forward and rearward door and panel, reduce the horizontal cross-section of the bath unit as one proceeds upwardly from rigidifying corners 24 and 23 towards corners 43 and 44, wherein the distance between the corners is least, thus providing a contoured shape for the vapour bath 10; said contoured shape allowing for alternative sizing of individual users, and further bringing the steam towards the body at the vapour bath unit's upper extremities. A collapsible roller 34 is illustrated in FIG. 3, allowing for the movement of the vapour bath from place to place without lifting, by grabbing the neck opening 40 and wheeling the unit about on roller device 34 as the vapour bath weighs 30 kilograms and is easily transported.

Figure 4:
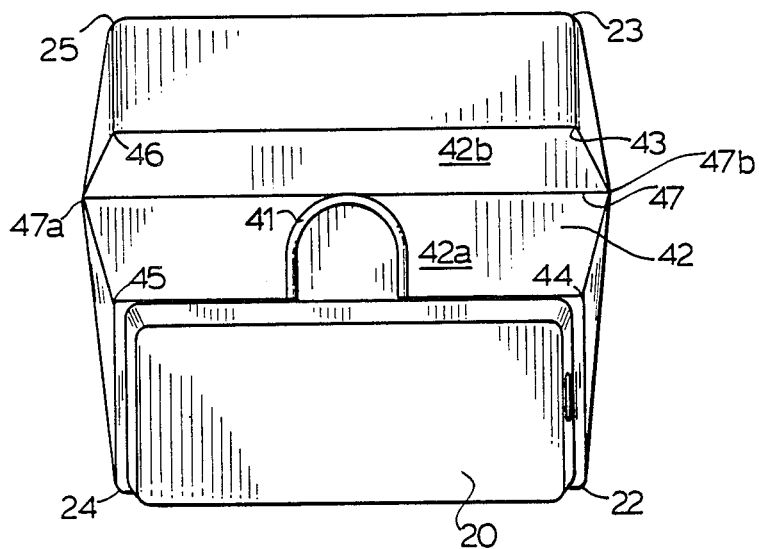
FIG. 4 is a side view of the portable vapour bath in a preferred embodiment of the invention.

Referring now to FIG. 4, vapour bath 10 is illustrated in top view illustrating centrally-located neck opening 40 and padding 41 being located forwardly on panel 42(a) adjacent rearward panel 42(b) joining at rigidifying seal or edge 47; said neck opening 40 extending rearwardly from forwardly-positioned door 20 wherein the head section of the door frame is centrally discontinuous to allow for the position of neck recess 40. Further, the sides of vapour bath 10 are contoured and rigidified by circumscribed rigidifying seal or edge 47 dividing the side panels in two, said bilateral panels slightly angling away from a normal vertical plane creating a contoured rigidifying structure.

Referring now to FIG. 5, vapour bath 10 is illustrated in cross-section (from a side view) in use wherein said individual "A" is comfortably seated upon contoured seat 50 within bath chamber 11 said seat centrally located and affixed to convex floor 55 by base 51 connected to cylindrical support 52, having affixed thereto fastening mechanism 54 whose opposite end is retained in an alternative number of holes 53 contained within seat support 50(a), thereby allowing the user freedom to adjust the seat height in a potentially indefinite number of positions for alternative embodiments. The convex shape of floor 55 in a preferred embodiment allows for the trapping of condensed moisture within the periphery of floor 55 which may be mopped up or drained through alternatively-positioned drain 55(a). Seat 50 is centrally located on floor 55, thereby allowing individual "A" adequate room to fit his/her knees within bath chamber 11 because door 20 is contoured to permit comfortable positioning of the knees and legs. Both the forward and rearward portions of the vapour bath taper from the seat towards the body in either direction. This contouring permits the steam to come in close contact with the body of the user at the more difficult locations such as the top of the back and front and neck areas without the need to provide an oversized high pressure steam generator which potentially could burn the user. The vapour generator 30 is illustrated having a separate structure affixed thereto to the bottom rearward panel of the unit, wherein said steam generator contains a reservoir 30(a), preferably having the capacity for six liters of water, in which a coil 32 is submerged, said coil one which is conventionally used in immersion heaters, having a power requirement of 1.5 to 1.8 kilowatts at 110 volts, including a temperature sensor to maintain the bath chamber temperature between 40 degrees to 45 degrees Celsius. A plug socket 33(a) is provided on the body of the generator 30 enabling safe electrical connection to be made. The immersed coil 32 is suitably located and thermostatically controlled such that only two-thirds of the contents of the reservoir 30(a) will be converted to vapour, preventing overheating of the coil and heater unit alike. The holes 31(b) compatibly aligned with holes 31 of vapour generator 30 are adjustable in cross-section allowing for variable rate and velocity of the steam generated. Alternatively, a thermostatically-controlled hot air generator may be used in place of vapour generator 30 having contained therein a fan to draw air over a heating element and safely heat and carry the air to the bath chamber 11. The vapours, steam or hot air generated will rise and set up a convection pattern in a counter-clockwise direction because a suitable space exists 360 degrees around the individual as a result of the contoured shape of vapour bath 10. Vapour will rise and be forced to contact upper body extremities by the contoured shape of the chamber and the variable adjustment 31(b) on the inlet ports 31(a). It is recommended that a towel be worn by the user about the neck to improve the seal at opening 40 and improve the effectiveness of the bath unit.

Further, the housing of the vapour bath is constructed from materials such as fibreglass reinforced plastics materials, which make it lightweight (30 kilograms), temperature resistant, readily shaped and alternatively coloured. As an alternative to a drain, a water collection tray may be provided with a duckboard cover on the floor to collect the condensing vapour and provide for quick and easy disposal thereof in areas where a drain is impractical, such as a living room. Arm rests and back rests may be provided with the seat as well as shelves and ledges embodied in the contoured internal walls of the vapour bath. Further, a portable shower device known in the art may be provided to the user. The vapour bath in a preferred embodiment is 115 cm. high, 90 cm. wide and 60 cm. deep at its extreme dimensions. The unit may be extended dimensionally to incorporate a multiplicity of users by adding the desired number of seats and corresponding neck openings. Further, infrared or alternative heaters may be substituted for the vapour generator in another embodiment.

As many changes can be made to the preferred embodiments without departing from the scope of the invention; it is intended that all matter contained herein be interpreted as illustrative of the invention and not in a limiting sense.

The embodiments of the invention in which an exclusive property or privilege is claimed are as follows:

1. A portable vapour bath comprising a double-tapered contoured superstructure and interior having a top, bottom, front, rear and plurality of sides; having disposed upon its front an opening closed by a closure member said closure member being disposed at an angle to both the normal horizontal and vertical planes; said front and rear having a top and bottom, said front and rear extending in planes substantially diverging from one another, each plane diverging from the normal vertical plane, proximate the top of the vapour bath to a position intermediate the top and bottom of said vapour bath whereat said front and rear extend in planes substantially converging towards one another and toward the vertical plane proximate the bottom of the vapour bath, said front being inclined from said top at an angle to both the normal horizontal and vertical planes away from the rear to a position intermediate its top and bottom and thereafter sloping to its bottom at an angle to both the normal horizontal and vertical planes in the opposite direction towards the rear; the rear sloping from its top at an angle to both the normal horizontal and vertical planes towards a position intermediate its top and bottom away from the front and thereafter sloping to its bottom in the opposite direction at an angle to both the normal horizontal and vertical planes towards the front; having disposed in its top an opening located above a seating means disposed upon the bottom of the vapour bath; having affixed adjacent the bottom thereof a separated source of wet or dry heat, wherein said bottom portion has at least one opening to allow entry of said wet or dry heat into the vapour bath; wherein said portable vapour bath will, because of its contoured shape, said contouring providing diverging and converging planes, ensure close contact of wet or dry heat forwardly, rearwardly, top and bottom, with the user's body located within the bath chamber upon a seat securely fastened to the interior bottom of said superstructure.

2. The portable vapour bath of claim 1, wherein the plurality of sides comprises at least one member per side, said sides having a top and bottom left and right, the sides sloping from their tops towards a position intermediate their tops and bottoms away from the opposite side thereof and thereafter sloping to their bottoms in the opposite direction towards the opposite side, the sides further sloping from their left towards a position intermediate their left and right away from the opposite side, and thereafter sloping to their right in the opposite direction towards the opposite side wherein said portable vapour bath will, because of its contoured shape, said contouring providing diverging and converging planes, ensure close contact of wet or dry heat forwardly, rearwardly, bottom, top, left and right with the user's body located within the bath chamber upon a seat securely fastened to the interior bottom of said superstructure.

3. The vapour bath of claims 1 or 2, wherein provision is made for more than one user.

4. The vapour bath of claims 1 or 2, wherein said wet or dry heat source is at least one electrically-operated, thermostatically-controlled vapour generator independently embodied and affixed to the rear of said vapour bath at the bottom thereof, having disposed upon its affixed surface a multiplicity of orifices in communication with orifices disposed upon the rear of the vapour bath and the bottom thereof; said vapour generator having a water tank into which a submersible thermostatically-controlled heating coil is situated, thereby preventing overheating and failure thereof, said coil being powered by an external power supply connected thereto upon the outer surface of the vapour generator, ensuring the safety of the user of the vapour bath, and said vapour generator further thermostatically controlled by the temperature within the bath chamber.

5. The vapour baths of claim 3, wherein said wet or dry heat source is at least one electrically-operated, thermostatically-controlled vapour generator independently embodied and affixed to the rear of said vapour bath at the bottom thereof, having disposed upon its affixed surface a multiplicity of orifices in communication with orifices disposed upon the rear of the vapour bath and the bottom thereof; said vapour generator having a water tank into which a submersible thermostatically-controlled heating coil is situated, thereby preventing overheating and failure thereof, said coil being powered by an external power supply connected thereto upon the outer surface of the vapour generator, ensuring the safety of the user of the vapour bath, and said vapour generator further thermostatically controlled by the temperature within the bath chamber.

6. The vapour bath of claims 1 or 2, wherein said bottom is convex in shape, containing alternatively a peripheral drain, or water tray and duckboard disposed thereupon, to handle the accumulation of condensate therein.

7. The vapour bath of claim 3, wherein said bottom is convex in shape, containing alternatively a peripheral drain, or water tray and duckboard disposed thereupon, to handle the accumulation of condensate therein.

8. The vapour bath of claim 4, wherein said bottom is convex in shape, containing alternatively a peripheral drain, or water tray and duckboard disposed thereupon, to handle the accumulation of condensate therein.

9. The vapour bath of claim 5, wherein said bottom is convex in shape, containing alternatively a peripheral drain, or water tray and duckboard disposed thereupon, to handle the accumulation of condensate therein.

10. The vapour bath of claim 5, wherein said multiplicity of orifices in communication with orifices disposed upon the bottom of the vapour bath and the rear thereof, are of variable and/or adjustable diameter.

11. The vapour bath of claim 9, wherein said multiplicity of orifices in communication with orifices disposed upon the bottom of the vapour bath and the rear thereof, are of variable and/or adjustable diameter.

* * * * *